(12) United States Patent
Huang et al.

(10) Patent No.: US 7,488,860 B2
(45) Date of Patent: Feb. 10, 2009

(54) METHOD FOR PRODUCING EXO-TETRAHYDRODICYCLOPENTADIENE USING IONIC LIQUID CATALYST

(75) Inventors: Ming-Yu Huang, Chiayi (TW); Jen-Chun Chang, Chiayi (TW); Jann-Chen Lin, Chiayi (TW); Kun-Hai Lin, Chiayi (TW); Jung-Chung Wu, Chiayi (TW)

(73) Assignee: Chinese Petroleum Corp., Taipei (TW)

( * ) Notice: Subject to any disclaimer, the term of this patent is extended or adjusted under 35 U.S.C. 154(b) by 324 days.

(21) Appl. No.: 11/519,878

(22) Filed: Sep. 13, 2006

(65) Prior Publication Data

US 2008/0064909 A1    Mar. 13, 2008

(51) Int. Cl.
*C07C 5/25* (2006.01)

(52) U.S. Cl. .................. 585/363; 585/377; 585/669

(58) Field of Classification Search .................. 585/669, 585/363, 377
See application file for complete search history.

(56) References Cited

U.S. PATENT DOCUMENTS

| | | | | |
|---|---|---|---|---|
| 3,381,046 | A | * | 4/1968 | Cohen et al. .................. 585/22 |
| 4,086,286 | A | * | 4/1978 | Janoski et al. ............... 585/360 |
| 4,107,223 | A | * | 8/1978 | Schneider et al. ........... 585/360 |
| 2006/0264642 | A1 | * | 11/2006 | Wassercheid et al. ....... 546/347 |

* cited by examiner

*Primary Examiner*—Glenn Caldarola
*Assistant Examiner*—In Suk Bullock
(74) *Attorney, Agent, or Firm*—Troxell Law Office, PLLC

(57) ABSTRACT

An exo-tetrahydrodicyclopentadiene is produced from endo-tetrahydrodicyclopentadiene through isomerization reaction. An acidic ionic liquid is used in the isomerization. The isomerization of endo-tetrahydrodicyclopentadiene gives a reaction conversion and a selectivity both higher than 99%. Besides, the ionic liquid used is environmental-friendly and recyclable.

11 Claims, 10 Drawing Sheets

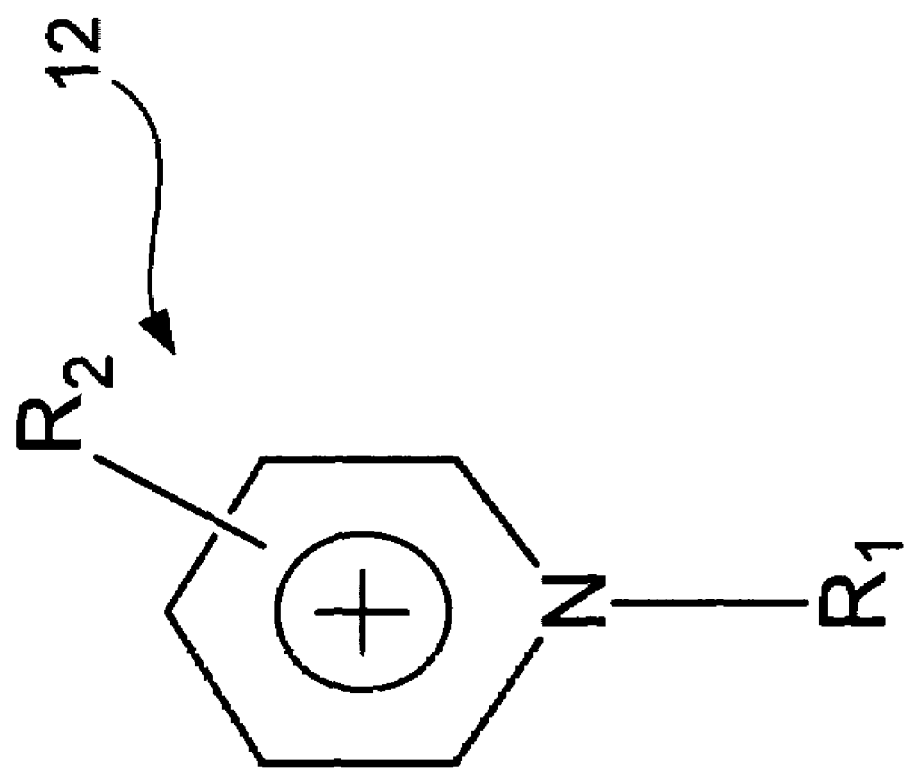

| Reaction temperature | 75°C | 67°C | 50°C |
|---|---|---|---|
| Reaction conversion of endo-tetrahydrodicyclopentadiene(%) | 93.9 | 89.6 | 81.1 |
| Selectivity of exo-tetrahydrodicyclopentadiene | 99.5 | 99.8 | 100 |

FIG.2

| Mole ratio | 1/25.6 | 1/12.8 | 1/1.28 |
|---|---|---|---|
| Reaction conversion of endo-tetrahydrodicyclopentadiene(%) | 36 | 81 | 99 |
| Selectivity of exo-tetrahydrodicyclopentadiene | 100 | 100 | 100 |

FIG.3

|  | BMIC | OMIC | HDMIC |
|---|---|---|---|
| Reaction conversion of endo-tetrahydrodicyclopentadiene(%) | 81.1 | 67 | 70 |
| Selectivity of exo-tetrahydrodicyclopentadiene | 100 | 100 | 100 |

FIG.5

|  | TEAC | PHC |
|---|---|---|
| Reaction conversion of endo-tetrahydrodicyclopentadiene(%) | 91 | 96 |
| Selectivity of exo-tetrahydrodicyclopentadiene | 100 | 99 |

FIG.6

|  | BMIB | PHB |
|---|---|---|
| Reaction conversion of endo-tetrahydrodicyclopentadiene(%) | 61.6 | 98.1 |
| Selectivity of exo-tetrahydrodicyclopentadiene | 100 | 99 |

FIG.7

METHOD FOR PRODUCING EXO-TETRAHYDRODICYCLOPENTADIENE USING IONIC LIQUID CATALYST

FIELD OF THE INVENTION

The present invention relates to a producing method; more particularly, relates to the isomerization of endo-tetrahydrodicyclopentadiene with acidic ionic liquids for obtaining exo-tetrahydrodicyclopentadiene.

DESCRIPTION OF THE RELATED ARTS

The exo-tetrahydrodicyclopentadiene is a kind of high-energy fuel. High-energy fuels are hydrocarbons with heating value higher than 118,000 Btu/gal. They could not be obtained from crude oil therefore, they are usually obtained from synthetic reactions; There are a lot of high-energy fuels, such as JP-4, W-5, R-J4, RJ-41, RJ-5, JP-9 and JP-10, where JP-10 gives higher heating value, lower freezing point and lower viscosity. Due to the unique properties of JP-10, it is often used to mix with other high-energy fuel to lower the freezing point and viscosity to be used in a jet or rocket engine.

A prior art, U.S. Pat. No. 3,381,046, "Jet and rocket fuel," is a method to produce exo-tetrahydrodicyclopentadiene. A sulfuric acid is used to obtain exo-tetrahydrodicyclopentadiene through an isomerization of endo-tetrahydrodicyclopentadiene. Although it is easy for the isomerization using such a strong acid, it involves side reactions, such as ring-opening, degradation and polymerization with many by-products. Besides, much black coke is produced; equipments may be corroded; and, used sulfuric acid has to be dealt with.

Another prior art is U.S. Pat. No. 4,086,284, "Isomerization of endo-tetrahydrodicyclopentadiene to a missile fuel diluent." Endo-tetrahydrodicyclopentadiene is processed through an isomerization to obtain exo-tetrahydrodicyclopentadiene with aluminum trichloride in a range of temperature, where the mole ratio of aluminum trichloride to the tetrahydrodicyclopentadiene is in the range between 0.001 and 0.75 and an inert solvent may also be used. But aluminum hydroxide may be formed after water washing or alkali washing; and, thus, profound sludge-like waste is produced.

Although the above two prior arts can process the isomerization of endo-tetrahydrodicyclopentadiene to obtain exo-tetrahydrodicyclopentadiene, a great amount of waste is produced or even the equipments may be worn out. Hence, the prior arts do not fulfill users' requests on actual use.

SUMMARY OF THE INVENTION

The main purpose of the present invention is to obtain exo-tetrahydrodicyclopentadiene through isomerization reaction using acidic ionic liquid catalyst with high reaction conversion and selectivity where the process is considered to be environmental-friendly and catalyst recyclization.

To achieve the above purpose, the present invention is a method for producing exo-tetrahydrodicyclopentadiene, where endo-tetrahydrodicyclopentadiene is processed with acidic ionic liquids to obtain exo-tetrahydrodicyclopentadiene through isomerization reaction; the ionic liquids are prepared with quaternary ammonium halide (or quaternary phosphonium halide) and aluminum trichloride; quaternary ammonium cations and quaternary phosphonium cations could be tetraalkylammonium, dialkylpyridinium, dialkylimidazolium or tetraalkylphosphonium; halide ions could be fluoride ion, chloride ion, bromide ion or iodide ion; a mole fraction of aluminum chloride in the ionic liquid is between 0.5 and 0.9; a mole ratio of the reaction feed stock to the ionic liquid is between 1/10 and 100/1; and the reaction temperature is between 25 and 120° C. Accordingly, a novel method for producing exo-tetrahydrodicyclopentadiene is obtained.

BRIEF DESCRIPTION OF THE DRAWINGS

The present invention will be better understood from the following detailed descriptions of the preferred embodiments according to the present invention, taken in conjunction with the accompanying drawings, in which FIG. 1A to FIG. 1D are the views showing the structures of tetraalkylammonium dialkylpyridinium, dialkylimidazolium and tetraalkylphosphonium; and FIG. 2 to FIG. 7 are the views showing the results of the first, the second, the third, the fourth, the fifth and the sixth preferred embodiments according to the present invention.

DESCRIPTIONS OF THE PREFERRED EMBODIMENTS

Figure 1A:
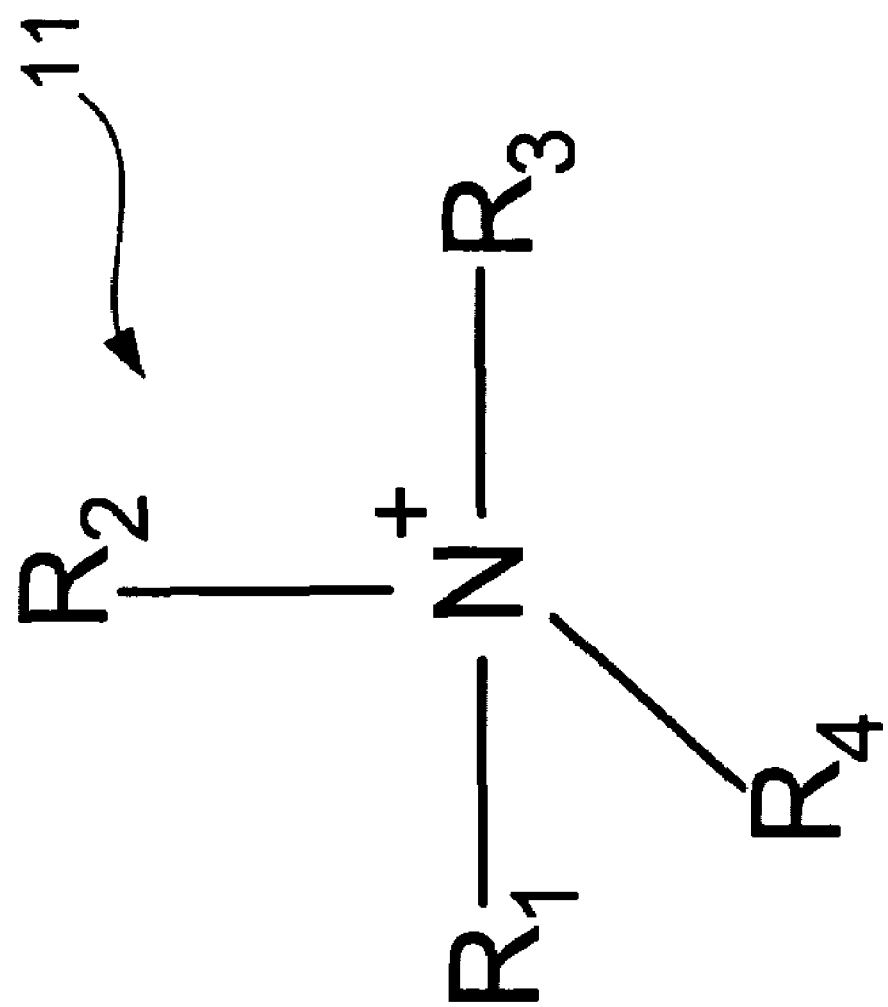
Figure 1C:
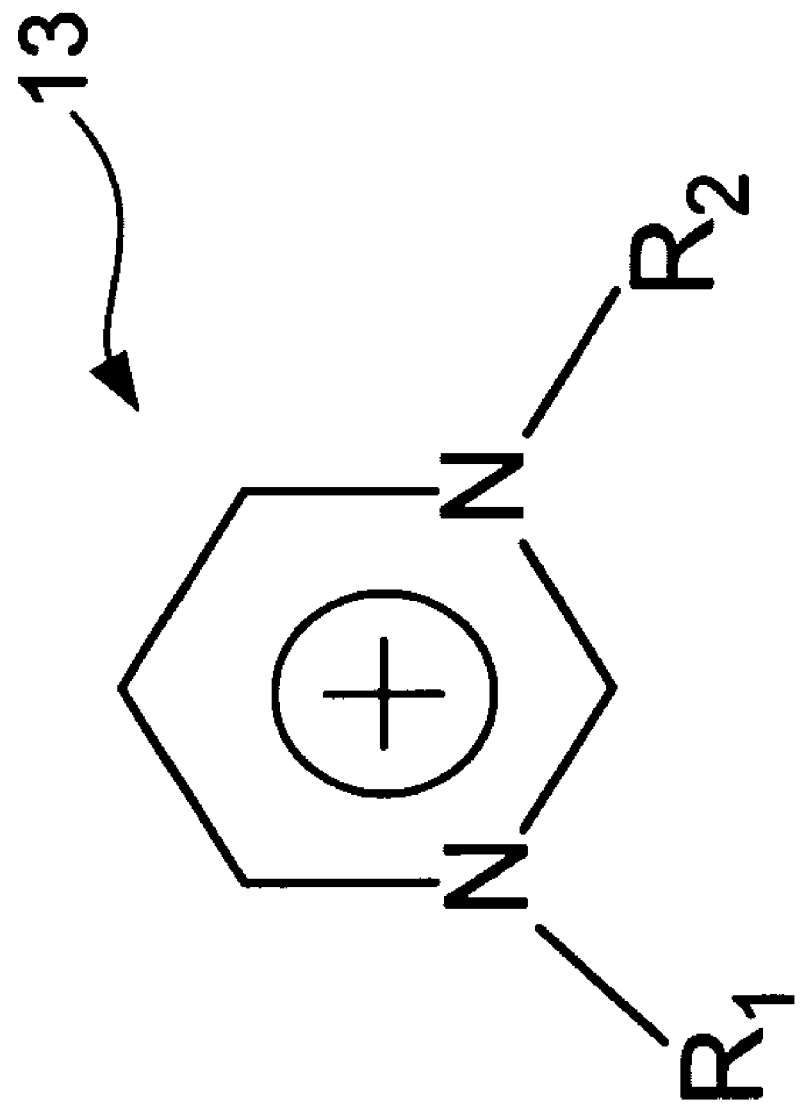
Figure 1D:
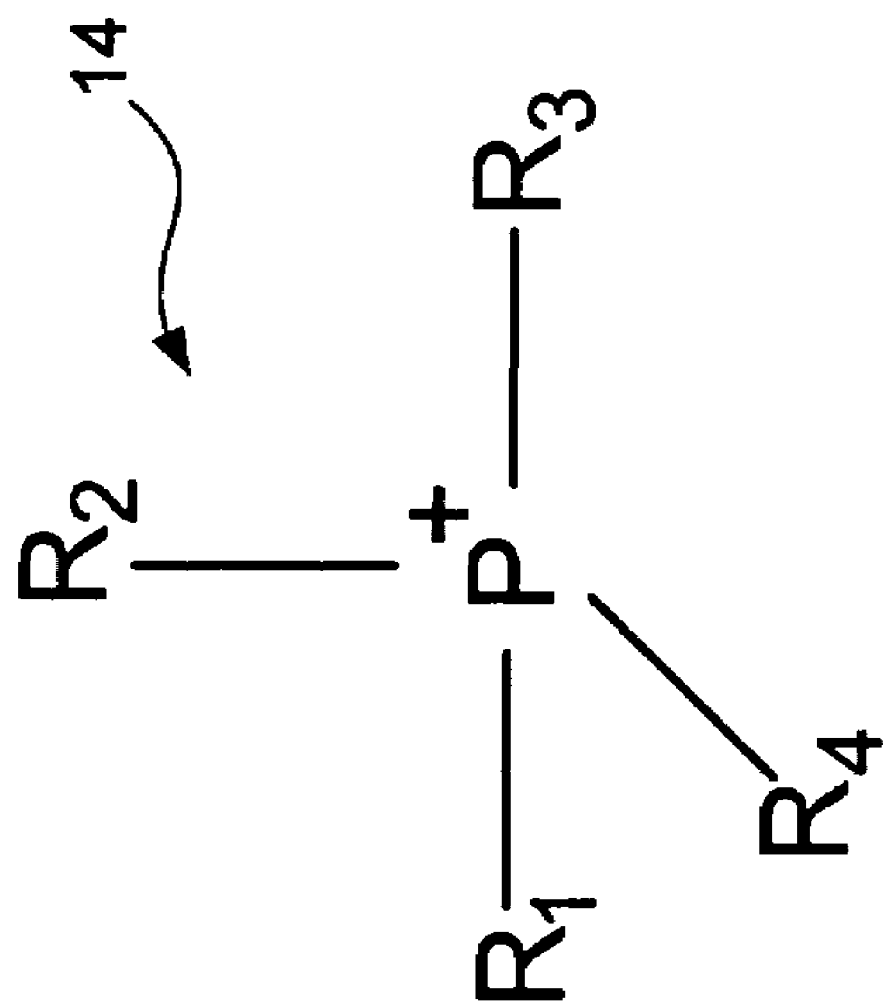

The following descriptions of the preferred embodiments are provided to understand the features and the structures of the present invention.

Please refer to FIG. 1A to FIG. 1D, which are views showing structures of tetraalkylammonium, dialkylpyridinium, dialkylimidazolium and tetraalkylphosphonium. As shown in the figures, the present invention is a method for producing exo-tetrahydrodicyclopentadiene, where a reaction feedstock of endo-tetrahydrodicyclopentadiene is used with chloroaluminate ionic liquid superacid for processing an isomerization to obtain an exo-tetrahydrodicyclopentadiene. Therein, the reaction feedstock comprises a solvent of hydrocarbon dissolving the endo-tetrahydrodicyclopentadiene; the concentration of endo-tetrahydrodicyclopentadiene is between 10 and 100 vol %; the mole fraction of chloroaluminate ionic liquid is between 0.5 and 0.9, where the preferred mole fraction is located between 0.55 and 0.7; a mole ratio of the reaction feedstock to the catalyst of chloroaluminmate ionic liquid is between 1/10 and 100/1, where the preferred mole ratio is located between 1/5 and 10/1; the chloroaluminate ionic liquid is prepared with quaternary ammonium halide (or quaternary phosphonium halide) and aluminum trichloride; the quaternary ammonium cations and quaternary phosphonium cations could be tetraalkyl ammonium, dialkylpyridinium, dialkylimidazolium or tetraalkylphosphonium; alkyl group in the tetraalkylammonium, dialkylpyridinium, dialkylimidazolium and tetraalkylphosphonium is $C_nH_{2n+1}$, whose n is a number between 0 and 18; halide ion in the tetraalkylammonium, dialkylpyridinium, dialkylimidazolium and tetraalkyl phosphonium could be fluoride ion, chloride ion, bromide ion or iodide ion; and the isomerization is processed under a temperature between 25 and 120° C., whose preferred temperature is located between 40 and 70° C.

The reaction feedstock is mainly made of endo-tetrahydrodicyclopentadiene; and the endo-tetrahydrodicyclopentadiene is made through a hydrogenation of endo-dicyclopentadiene, whose catalyst is an Engelhard nickel catalyst. When preparing the endo-tetrahydrodicyclopentadiene, the endo-dicyclopentadiene is dissolved in a heptane with a volume ratio of 1:1; and then pumped into a reaction tube with the Engelhard nickel catalyst (having 60 wt % of nickel) for processing a hydrogenation reaction.

The chloroaluminate ionic liquid is prepared in a glove box filled with nitrogen. A two-necked round bottomed flask with a three-way stopcock having stirrer magnet is deposed in the glove box together with quaternary ammonium halide and aluminum trichloride. Then the quaternary ammonium halide and the aluminum trichloride is weighted and poured into the two-necked round bottomed flask with stirring. And then the two-necked round bottomed flask having a chloroaluminate ionic liquid is taken out of the glove box to be equipped with a condenser under a nitrogen gas environment. The two-necked round bottomed flask is then processed through an oil bath under a pre-set temperature with stirring.

When processing the isomerization reaction, a certain amount of the reaction feedstock is sucked into the two-necked round bottomed flask having the chloroaluminate ionic liquid, the stirrer magnet and the condenser. Sampling is carried out at intervals for gas chromatograph analysis.

Embodiment 1

Please refer to FIG. 2, which is a view showing a result of a first preferred embodiment according to the present invention. As shown in the figure, a chloroaluminate ionic liquid is prepared at first. In a glove box, 0.8 g (0.00458 moles) of 1-butyl-3-methylimidazolium chloride (BMIC) and 0.916 g (0.00687 moles) of aluminum tri chloride are used to prepare a chloroaluminate ionic liquid. Then a two-necked round bottomed flask loaded with the chloroaluminate ionic liquid is taken out of the glove box to be equipped with a condenser. The flask is then processed through an oil bath under 50° C. A 16 g of reaction feedstock is injected into the flask and stirred with 400 rpm.

Then the product after the reaction is taken out to be analyzed with a gas chromatograph. The analysis shows that: the isomerization for 6 hrs at 50° C. obtains a reaction conversion of endo-tetrahydrodicyclopentadiene 21 as 81.1% a and a selectivity of exo-tetrahydrodicyclopentadiene 22 as 100%.

Then the chloroaluminate ionic liquid prepared is processed through an oil bath under 67° C. and the other oil bath under 75° C. separately to be poured with 16 g of reaction feedstock for an isomerization with a stirring speed of 400 rpm. The reaction result is analyzed with a gas chromatograph and shows that the isomerization for 6 hrs at 67° C. and 75° C. respectively obtains reaction conversions of endo-tetrahydrodicyclopentadiene 21 as 89.6% and 93.9% and selectivity of exo-tetrahydrodicyclopentadiene 22 as 99.8% and 99.5%.

Embodiment 2

Please refer to FIG. 3, which is a view showing a result of a second preferred embodiment. As shown in the figure, two sets of chloroaluminate ionic liquid is prepared. In a glove box, 0.4 g (0.00229 moles) of BMIC and 0.458 g (0.00343 moles) of aluminum trichloride are used to prepare a set of chloroaluminate ionic liquid; and, 8 g (0.0458 moles) of BMIC and 9.16 g (0.0687 moles) of aluminum trichloride are used to prepare the other set of chloroaluminate ionic liquid. These two sets of chloroaluminate ionic liquid separately have mole ratio of 1/25.6 and 1/1.28 to a reaction feedstock. Both of the flasks are processed through oil bath under 50° C. A 16 g of reaction feedstock is injected into each flask for an isomerization with a stirring speed of 400 rpm.

After 6 hrs of reaction, a result of the chloroaluminate ionic liquid having a mole ratio of 1/25.6 to the reaction feedstock shows a reaction conversion of endo-tetrahydrodicyclopentadiene 31 as 36% and a selectivity of exo-tetrahydrodicyclopentadiene 32 as 100%. A result of the other chloroaluminate ionic liquid having a mole ratio of 1/1.28 to the reaction feedstock shows a reaction conversion of endo-tetrahydrodicyclopentadiene 31 as 99% and a selectivity of exo-tetrahydrodicyclopentadiene 32 as 100%.

Embodiment 3

Figure 4:
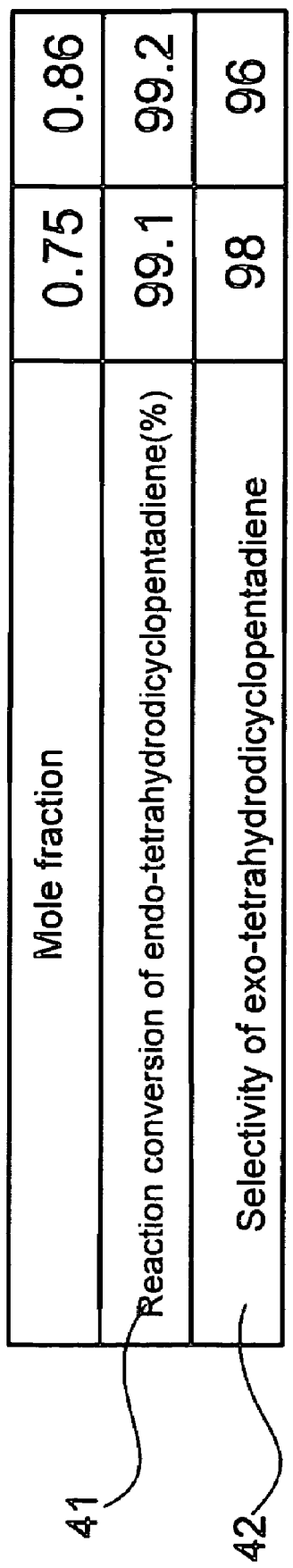

Please refer to FIG. 4, which is a view showing a result of a third preferred embodiment. As shown in the figure, two sets of chloroaluminate ionic liquid is prepared, where 0.8 g (0.00458 moles) of BMIC and 1.832 g (0.0137 moles) of aluminum trichloride are used to prepare a set of chloroaluminate ionic liquid; and, 0.8 g (0.00458 moles) of BMIC and 3.75 g (0.0281 moles) of aluminum tri chloride are used to prepare the other set of chloroaluminate ionic liquid. Aluminum chloride in the two sets of chloroaluminate ionic liquid separately have mole ratio of 0.75 and 0.86. Both of the flasks are processed through oil bath under 50° C. A 16 g of reaction feedstock is injected into each flask for anisomerization with a stirring speed of 400 rpm.

After 6 hrs of reaction, a result of the chloroaluminate ionic liquid having a mole ratio of 0.75 of aluminum chloride shows a reaction conversion of endo-tetrahydrodicyclopentadiene 41 as 99.1% and a selectivity of exo-tetrahydrodicyclopentadiene 42 as 98%. A result of the other chloroaluminate ionic liquid having a mole ratio of 0.86 of aluminum chloride shows a reaction conversion of endo-tetrahydrodicyclopentadiene 41 as 99.2% and a selectivity of exo-tetrahydrodicyclopentadiene 42 as 96%.

Embodiment 4

Please refer to FIG. 5, which is a view showing a result of a fourth preferred embodiment. As shown in the figure, 1.051 g (0.00458 moles) of 1-octyl-3-methylimidazolium chloride (OMIC) and 0.916 g (0.00687 moles) of aluminum trichloride are used to prepare a set of chloroaluminate ionic liquid; and, 1.573 g (0.00458 moles) of 1-hexadecyl-3-methylimidazolium chloride (HDMIC) and 0.916 g (0.0687 moles) of aluminum trichloride are used to prepare the other set of chloroaluminate ionic liquid. Both of the flasks are processed through oil bath under 50° C. A 16 g of reaction feedstock is injected into each flask for an isomerization with a stirring speed of 400 rpm.

After 6 hrs of reaction, a result of the chloroaluminate ionic liquid using OMIC shows a reaction conversion of endo-tetrahydrodicyclopentadiene 51 as 67% and a selectivity of exo-tetrahydrodicyclopentadiene 52 as 100%. A result of the other chloroaluminate ionic liquid using HDMIC shows a reaction conversion of endo-tetrahydrodicyclopentadiene 51 as 70% and a selectivity of exo-tetrahydrodicyclopentadiene 52 as 100%. Accordingly, a result of the chloroaluminate ionic liquid using BMIC having the same mole ratio (0.00458 moles in 0.0687 moles) shows a reaction conversion of endo-tetrahydrodicyclopentadiene 51 as 81% and a selectivity of exo-tetrahydrodicyclopentadiene 52 as 100%.

Embodiment 5

Please refer to FIG. 6, which is a view showing a result of a fifth preferred embodiment. As shown in the figure, 0.63 g (0.00458 moles) of triethylamine hydrochloride (TEAC) and 0.916 g (0.00687 moles) of aluminum trichloride are used to prepare a set of chloroaluminate ionic liquid; and, 0.085 g (0.00458 moles) of pyridine hydrochloride (PHC) and 0.916 g (0.0687 moles) of aluminum trichloride are used to prepare the other set of chloroaluminate ionic liquid. Both of the flasks are processed through oil bath under 50° C. A 16 g of reaction feedstock is injected into each flask for an isomerization with a stirring speed of 400 rpm.

After 6 hrs of reaction, a result of the chloroaluminate ionic liquid using TEAC shows a reaction conversion of endo-tetrahydrodicyclopentadiene 61 as 91% and a selectivity of exo-tetrahydrodicyclopentadiene 62 as 100%. A result of the other chloroaluminate ionic liquid using HDMIC shows a reaction conversion of endo-tetrahydrodicyclopentadiene 61 as 96% and a selectivity of exo-tetrahydrodicyclopentadiene 62 as 99%.

Embodiment 6

Please refer to FIG. 7, which is a view showing a result of a sixth preferred embodiment. As shown in the figure, 0.7328 g (0.00458 moles) of pyridine hydrobromide (PHB) and 0.916 g (0.00687 moles) of aluminum trichloride are used to prepare a set of chloroaluminate ionic liquid; and, 1.004 g (0.00458 moles) of 1-butyl-3-methylimidazolium bromide (BMIB) and 0.916 g (0.0687 moles) of aluminum trichloride are used to prepare the other set of chloroaluminate ionic liquid. Both of the flasks are processed through oil bath under 50° C. A 16 g of reaction feedstock is injected into each flask for an isomerization with a stirring speed of 400 rpm.

After 6 hrs of reaction, a result of the chloroaluminate ionic liquid using BMIB shows a reaction conversion of endo-tetrahydrodicyclopentadiene 71 as 61.6% and a selectivity of exo-tetrahydrodicyclopentadiene 72 as 100%. A result of the other chloroaluminate ionic liquid using PHC shows a reaction conversion of endo-tetrahydrodicyclopentadiene 71 as 98.1% and a selectivity of exo-tetrahydrodicyclopentadiene 72 as 99%.

To sum up, the present invention is a method for producing exo-tetrahydrodicyclopentadiene, where the exo-tetrahydrodicyclopentadiene produced according to the present invention has a reaction conversion and a selectivity both higher than 99%; and the process is environmental-friendly and catalyst-recyclable.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method for producing exo-tetrahydrodicyclopentadiene, said method having a reaction feedstock of endo-tetrahydrodicyclopentadiene to be processed through an isomerization with a catalyst of chloroaluminate ionic liquid, wherein said chloroaluminate ionic liquid has a mole fraction between 0.5 and 0.9;
wherein a mole ratio of said reaction feedstock to said catalyst is between 1/10 and 100/1; and
wherein said isomerization is processed under a temperature between 25 and 120° C.

2. The method according to claim 1,
wherein said reaction feedstock has a solvent of a hydrocarbon.

3. The method according to claim 1,
wherein said reaction feedstock of said endo-tetrahydrodicyclopentadiene has an amount ratio between 10 and 100 volume percents.

4. The method according to claim 1,
wherein said chloroaluminate ionic liquid is prepared with qua ternary ammonium halide and aluminum trichloride.

5. The method according to claim 4,
wherein said quaternary ammonium halide has a quaternary ammonium cation selected from a group consisting of tetra alkyl ammonium, dialkylpyridinium, and dialkylimidazolium.

6. The method according to claim 5,
wherein alkyl group in said tetraalkylammonium, said dialkylpyridinium, and said dialkylimidazolium is $C_nH_{2n+1}$; and
wherein said n is a number between 0 and 18.

7. The method according to claim 4,
wherein said quaternary ammonium halide has a halide ion selected from a group consisting of fluoride ion, chloride ion, bromide ion and iodide ion.

8. The method according to claim 1,
wherein said chloroaluminate ionic liquid is prepared with quaternary phosphonium halide and aluminum trichloride.

9. The method according to claim 8,
wherein said quaternary phosphonium halide has a quaternary phosphonium cation of tetraalkylphosphonium.

10. The method according to claim 9,
wherein alkyl group of said tetraalkylphosphonium is $C_nH_{2n+1}$; and
wherein said n is a number between 0 and 18.

11. The method according to claim 8,
wherein said quaternary phosphonium halide has a halide ion selected from a group consisting of fluoride ion, chloride ion, bromide ion and iodide ion.

* * * * *